United States Patent
Korhummel

(10) Patent No.: US 10,601,121 B2
(45) Date of Patent: Mar. 24, 2020

(54) SLOT ANTENNA FOR IN-BODY ISM-BAND COMMUNICATION

(71) Applicant: Verily Life Sciences LLC, South San Francisco, CA (US)

(72) Inventor: Sean Korhummel, San Carlos, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/969,976

(22) Filed: May 3, 2018

(65) Prior Publication Data
US 2018/0331422 A1    Nov. 15, 2018

Related U.S. Application Data

(60) Provisional application No. 62/503,515, filed on May 9, 2017.

(51) Int. Cl.
    *H01Q 13/10*   (2006.01)
    *H01Q 1/27*    (2006.01)
    (Continued)

(52) U.S. Cl.
    CPC ............. *H01Q 1/27* (2013.01); *A61B 5/0031* (2013.01); *A61B 5/076* (2013.01); *A61B 5/6861* (2013.01);
    (Continued)

(58) Field of Classification Search
    CPC ........ H01Q 13/16; H01Q 13/10; H01Q 3/443; H01Q 7/00; H01Q 13/18; H01Q 21/064;
    (Continued)

(56) References Cited

U.S. PATENT DOCUMENTS

| 7,903,043 B2 | 3/2011 | Rawat et al. |
| 8,515,559 B2 | 8/2013 | Roberts et al. |

(Continued)

FOREIGN PATENT DOCUMENTS

KR    101428928    8/2014

OTHER PUBLICATIONS

International Application No. PCT/US2018/031426, "International Search Report and Written Opinion", dated Jul. 30, 2018, 14 pages.

*Primary Examiner* — Binh B Tran
(74) *Attorney, Agent, or Firm* — Kilpatrick Townsend & Stockton LLP

(57) ABSTRACT

Examples of implantable devices having a hermetically-sealed, metal container are disclosed. In one example, the implantable device has a Bluetooth Low Energy ("BLE") beacon inside the hermetically-sealed, metal container. The hermetically-sealed, metal container may have a micro-strip type transmission line on an internal side of the container such that the container acts as the ground plane of the micro-strip transmission line. A slot at a specific location and having specific characteristics (such as shape, length, and/or width) may be cut into the ground plane of the micro-strip to act as a radiator. Thus, the size of implantable devices can be reduced by using a slot antenna in the hermetically-sealed, metal container. Such a device implanted in a suitable location and at a suitable depth in a user can communicate with an external computing device, such as a smartphone held in the user's hand.

35 Claims, 5 Drawing Sheets

(51) Int. Cl.
*H01P 3/08* (2006.01)
*H01Q 1/22* (2006.01)
*A61B 5/07* (2006.01)
*A61B 5/00* (2006.01)
*H01Q 13/00* (2006.01)
*A61B 5/01* (2006.01)
*H04W 4/80* (2018.01)
*A61B 5/145* (2006.01)
*A61B 5/055* (2006.01)
*H01Q 13/16* (2006.01)

(52) U.S. Cl.
CPC .............. *H01P 3/081* (2013.01); *H01Q 1/22* (2013.01); *H01Q 1/2291* (2013.01); *H01Q 1/273* (2013.01); *H01Q 13/10* (2013.01); *H01Q 13/106* (2013.01); *A61B 5/01* (2013.01); *A61B 5/055* (2013.01); *A61B 5/14503* (2013.01); *A61B 5/14539* (2013.01); *A61B 5/14542* (2013.01); *A61B 2562/0247* (2013.01); *A61B 2562/162* (2013.01); *A61B 2562/18* (2013.01); *H01Q 13/16* (2013.01); *H04W 4/80* (2018.02)

(58) Field of Classification Search
CPC ............. H01Q 21/0043; H01Q 21/005; H01Q 21/0056; H01Q 21/0062
USPC ......................................... 343/746, 767–771
See application file for complete search history.

(56) References Cited

U.S. PATENT DOCUMENTS

| | | |
|---|---|---|
| 9,259,582 B2 | 2/2016 | Joshi et al. |
| 9,318,798 B2 | 4/2016 | Crivelli et al. |
| 9,409,018 B2 | 8/2016 | Tourrel et al. |
| 2010/0161002 A1* | 6/2010 | Aghassian ......... A61N 1/37229 607/60 |
| 2012/0276856 A1* | 11/2012 | Joshi ................... A61N 1/37229 455/73 |
| 2013/0002496 A1 | 1/2013 | Utsi et al. |
| 2014/0180262 A1* | 6/2014 | Farra ..................... A61B 5/076 604/890.1 |
| 2016/0359222 A1 | 12/2016 | Li et al. |
| 2017/0281955 A1* | 10/2017 | Maile ................... A61B 5/0422 |

* cited by examiner

SLOT ANTENNA FOR IN-BODY ISM-BAND COMMUNICATION

CROSS-REFERENCE TO RELATED APPLICATIONS

The present application claims priority to Provisional Application No. 62/503,515, filed on May 9, 2017, and entitled "Slot Antenna For In-Body Ism-Band COMMUNICATION," the entirety of which is hereby incorporated by reference herein.

FIELD

The present application generally relates to transmitters and more generally relates to implantable in-body industrial, scientific, and medical ("ISM")-band transmitters.

BACKGROUND

Portable computing devices, such as laptop computers, tablets, cell phones, smartphones, wearable devices, and other Internet-capable devices are prevalent in numerous aspects of modern life. Bluetooth is one wireless technology standard for exchanging data between portable computing devices over a short range. For example, Bluetooth may be used to connect a cell phone to a wireless headset, possibly allowing for hands-free use of the phone. Numerous applications have allowed Bluetooth to become a standard wire-replacement protocol. In various applications, Bluetooth has become an attractive low-cost, low power consumption solution for wireless data exchange.

SUMMARY

Various examples of slot antennas for in-body ISM-band communication are described herein.

One example disclosed implantable an industrial, scientific, and medical ("ISM")-band device comprises a hermetically-sealed container having disposed within the hermetically-sealed container at least: an ISM-band transmitter; a microwave dielectric substrate; and a micro-strip transmission line located on the microwave dielectric substrate. The hermetically-sealed container can define a slot in an interior side of the hermetically-sealed container. The slot may have a depth less than a thickness of the interior side of the hermetically-sealed container. The slot can cross the micro-strip transmission line.

The ISM-band transmitter may be an S-band transmitter. The ISM-band transmitter may be a Bluetooth transmitter such as a Bluetooth Low Energy ("BLE") transmitter. The ISM-band transmitter can be positioned on near an end of the micro-strip transmission line. The slot may be configured to transmit a radio frequency ("RF") signal from the ISM-band transmitter (such as a BLE transmitter) to an external computing device at a frequency between 2400 MHz and 2483.5 MHz. The hermetically-sealed container may have cylindrical shape. The hermetically-sealed container can have a diameter between 10 millimeters and 40 millimeters. The hermetically-sealed container can have a height between 3 millimeters and 5 millimeters.

The microwave dielectric substrate may be aluminum oxide or may include aluminum oxide. The micro-strip transmission line can be copper deposited on the microwave dielectric substrate. The microwave dielectric substrate may have a thickness between 0.11 millimeters and 0.15 millimeters. The micro-strip transmission line can have a thickness between 0.2 millimeters and 0.3 millimeters.

The slot may have a width between 100 microns and 600 microns. In examples, the slot has a width between 120 microns and 140 microns. The slot can have a length between 16 millimeters and 28 millimeters. The slot may be perpendicular to the micro-strip transmission line. The slot can cross the micro-strip transmission line at a middle of the micro-strip transmission line. The slot can cross the micro-strip transmission line towards an end of the micro-strip transmission line. In examples, the slot does not have a gel and thus the slot is not filled with any gel.

The hermetically-sealed container may be a titanium container. The hermetically-sealed container can provide a ground plane for the micro-strip transmission line. The slot can provide a far-field radiator.

In examples, the implantable ISM-band device does not comprise an electronic component outside of the hermetically-sealed container. For example, the implantable ISM-band device does not comprise an antenna external to the hermetically-sealed container in some examples. In some examples, the implantable ISM-band device does not comprise an inverted F antenna, does not comprise a monopole antenna, and does not comprise an electrically small dipole antenna.

In examples, the hermetically-sealed container internally contains an electrical component on a same plane as the micro-strip transmission line. In examples, the slot provides a slot antenna and having the electrical component on the same plane as the micro-strip transmission line increases a gain of the slot antenna. The electrical component may be a microprocessor and/or a tuning circuit.

The implantable ISM-band device is configured to be implantable in a human body. For example, the implantable ISM-band device may be configured to be implanted in a user's skin. For example, the ISM-band device may be implantable approximately 3 millimeters below a skin surface in a user. As another example, the ISM-band device may be implantable between 1 millimeter and 10 millimeters below a skin surface in a user. The implantable ISM-band device may be configured to be implanted in a user's muscle. For example, the ISM-band device may be implantable approximately 3 millimeters below a muscle surface in a user. As another example, the ISM-band device may be implantable between 1 millimeter and 6 millimeters below a muscle surface in a user. In these examples, the implanted ISM-band device can be configured to transmit signals to an external (i.e., not implanted) computing device. The external computing device can be a smartphone, a tablet, an electronic wristband, an electronic armband, an electronic ankle band, an electronic necklace, or another portable external computing device. The implanted ISM-band device may transmit signals to the external computing device using a Bluetooth-compatible frequency. In examples, the implanted ISM-band device can receive signals from the external computing device using a Bluetooth-compatible device. Signals received by the implanted ISM-band device from the external computing device can include configuration data to configure the implanted device.

One example disclosed system comprises an implantable ISM-band device. In this example, the implantable ISM-band device comprises a hermetically-sealed container internally having disposed within the hermetically-sealed container at least: a microwave dielectric substrate; a micro-strip transmission line located on the microwave dielectric substrate, wherein the hermetically-sealed container acts as a ground plane for the micro-strip transmission line; an industrial, scientific, and medical ("ISM")-band transmitter positioned near an end of the micro-strip transmission line; and a sensor. The hermetically-sealed container can define a slot in an interior side of the hermetically-sealed container. The slot may cross the micro-strip transmission line. The slot can be configured to transmit a radio frequency ("RF") signal from the ISM-band transmitter to an external computing device. The RF signal may correspond to sensor data from the sensor. The ISM-band transmitter may be a Bluetooth Low Energy ("BLE") transmitter and the RF signal can have a frequency between 2400 MHz and 2483.5 MHz.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
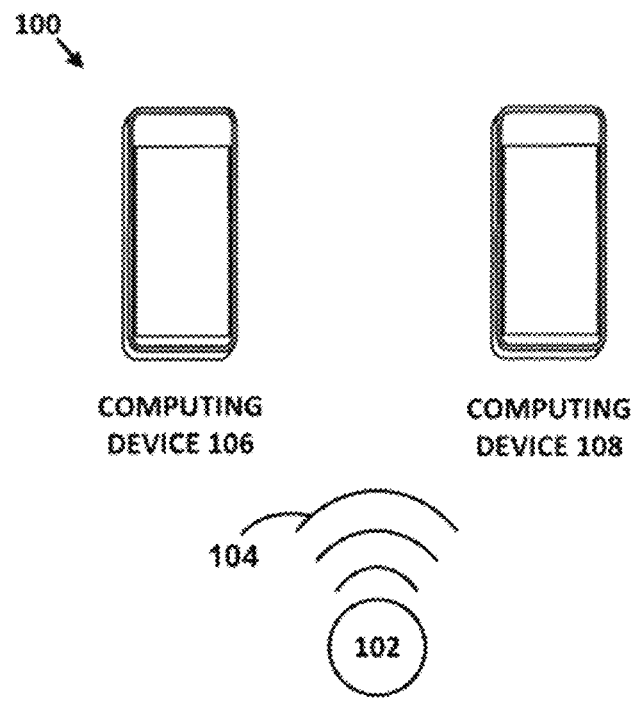
FIG. 1 shows computing devices located in proximity to a beacon according to an example.

Examples are described herein in the context of a slot antenna for in-body ISM-band communication. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of a Slot Antenna for in-Body ISM-Band Communication

In one illustrative example, a hermetically-sealed ISM-band device is implantable into a user's body. For example, the ISM-band device may be implanted in a user's chest at approximately 3 millimeters below the user's skin. In one example, the ISM-band device is cylindrical having a diameter of approximately 30 millimeters and a height of approximately 5 mm.

In this example, the implanted device is configured to transmit signals to a user's smartphone. For example, if the ISM-band device is a BLE transmitter, then the ISM-band device may be configured to transmit signals to a smartphone in accordance with a Bluetooth Core Specification supporting BLE. The implanted device can transmit signals having sensor data (e.g., temperature, pressure, oxygen level, and/or pH level, etc.) to the smartphone. The sensor data may be received from sensor(s) (e.g., temperature sensor, pressure sensor, oxygen sensor, and/or pH sensor, etc.) in the hermetically-sealed ISM-band device.

In this example, the ISM-band device has a hermetically-sealed container and the other components of the ISM-band device are located within the hermetically-sealed container. For example, the ISM-band device's communication components (such as an ISM-band transmitter) can be located within the hermetically-sealed container.

Moreover, in this example, the hermetically-sealed container is made of titanium and acts as a radiation device. A micro-strip transmission line on a microwave dielectric substrate can be located inside the hermetically-sealed container and the container may act as the ground plane of the micro-strip transmission line. For example, the micro-strip may be a straight-line trace of approximately 0.25 millimeters thick copper on an approximately 0.13 millimeters thick thermoset microware material (such as TMM10®) located inside the hermetically-sealed container. An ISM-band transmitter (such as a BLE transmitter, an S-band transmitter, or another suitable ISM-band transmitter) may be located near an end of the straight-line trace inside the hermetically-sealed container. In this example, a slot having a width of approximately 127 microns and a length of approximately 20 millimeters is cut into an inside side of the hermetically-sealed container. The slot has a depth that is less than the thickness of the inside side of the hermetically-sealed container such that the container remains airtight. Thus, the slot is not deep enough to go all the way through the inside side of the container.

The slot crosses the micro-strip transmission line and may be positioned in the middle of the micro-strip transmission line. The slot acts as a far-field radiator. Thus, the ISM-band device does not require an antenna (such as an inverted F antenna, a monopole antenna, an electrically small dipole antenna, etc.) typically used for consumer applications which reduces the required size of the ISM-band device.

This illustrative example is given to introduce the reader to the general subject matter discussed herein and the disclosure is not limited to this example. The following sections describe various additional non-limiting examples.

Bluetooth continues to grow as the standard wire-replacement protocol, and remains particularly attractive due to its protocols designed for low power consumption. Specifically, Bluetooth Low Energy ("BLE"), an extension of Bluetooth technology, may be attractive in applications where low power consumption may be advantageous. Accordingly, in some examples, an ISM-band device has a BLE transmitter such as a BLE beacon. In such examples, the ISM-band device may be referred to herein as a BLE device.

In particular, BLE provides protocols for low power devices to communicate with multiple other devices. For example, consider a device that can be powered by one or more batteries. Further, consider that the device may be used in an application where replacing or recharging the one or more batteries may not be easily achievable. Accordingly, the device may be a low power device to preserve the charge of its power source. As such, the device may utilize BLE's protocols for communicating with other computing devices (e.g., smartphone, laptops, and wearable computing devices). In an example, the low power device may utilize BLE protocols to transmit data (e.g., sensor data) to a computing device.

Referring now to FIG. 1, this figure illustrates an example scenario 100 of a device utilizing ISM-band compatible protocols. For example, the device may utilize BLE protocols in some examples. ISM-band compatible protocols, such as Bluetooth protocols or BLE protocols, may be carried out by a low power device 102 (also referred to herein as a "beacon"), which may include one or more sensors (such as an electrode, oxygen sensor, pH sensor, pressure sensor, temperature sensor, etc.). More specifically, the beacon 102 may include an ISM-band device or module (such as a BLE device or module), which may transmit and/or receive a signal 104 according to ISM-band compatible protocols). The power source of an ISM-band device may be one or more batteries. In some examples, the one or more batteries may be the one or more batteries of the beacon 102 in which the ISM-band device is incorporated. Further, the beacon 102 may transmit, according to ISM-band compatible protocols (such as BLE protocols), the signal 104 to the computing devices 106 and/or 108. In examples, signal 104 includes sensor data from one or more sensors in low power device 102.

However, it should be understood that the arrangement for the beacon 102 provided in FIG. 1 is for purposes of illustration only. For example, the beacon 102 may be included in any suitable device, such as a device with a hermetically-sealed, implantable container. Further, in some examples, the beacon 102 may transmit a signal 104 to more than or fewer than two computing devices.

In some examples, the beacon 102 can be implanted in a user. For example, the beacon 102 can be implanted under a user's skin. In such implanted examples, the beacon 102 can be enclosed in a hermetically-sealed container. The container may be a metal container. An interior of the container can have a micro-strip transmission line. In this example, the metal container can act as the ground plane of the micro-strip transmission line. Further, in examples, a slot may be cut into the ground plane of the micro-strip (and thus the slot is cut into the metal container) to act as a far-field radiator. In this example, the tuning of the impedance, quality of radiation, and/or polarization of the radiation depends on the location and characteristics (e.g., shape, length, width, etc.) of the slot in the metal container. Further, in this example, an antenna (such as an inverted F antenna, a monopole antenna, an electrically small dipole antenna, etc.) is not required because the slot in the hermetically-sealed metal container acts as the antenna thus saving space.

In scenario 100, each of the computing devices 106 and 108 may include an ISM-band module (such as a Bluetooth module), which may perform a scan to search for other compatible devices and/or for signals from compatible devices. For example, if an ISM-band module is a Bluetooth module, then the Bluetooth module may perform a Bluetooth scan to search for other Bluetooth devices and/or for signals from Bluetooth devices. In this example, the computing devices 106 and 108 may scan for Bluetooth devices in order to pair with a Bluetooth device that is within a range of the Bluetooth scan of the computing devices. In other examples, at least one of the computing devices 106 and 108 may receive a signal from a Bluetooth device without pairing with the Bluetooth device. For example, at least one of the computing devices may receive a Bluetooth signal, e.g., signal 104, from the beacon 102 without pairing with the beacon 102.

Furthermore, scenario 100 may be a scenario where low power consumption by the beacon 102 is desirable. For example, the power source of the beacon 102 may have limited charge. In such a scenario, low power consumption by the beacon 102 may be desirable to extend the life of the power source. Generally, the power consumption of an ISM-band device, such as a BLE device, may be governed by the configuration of the ISM-band device and/or the hardware of the ISM-band device. Accordingly, the ISM-band devices disclosed herein may be described in relation to at least decreasing power consumption.

Figure 2:
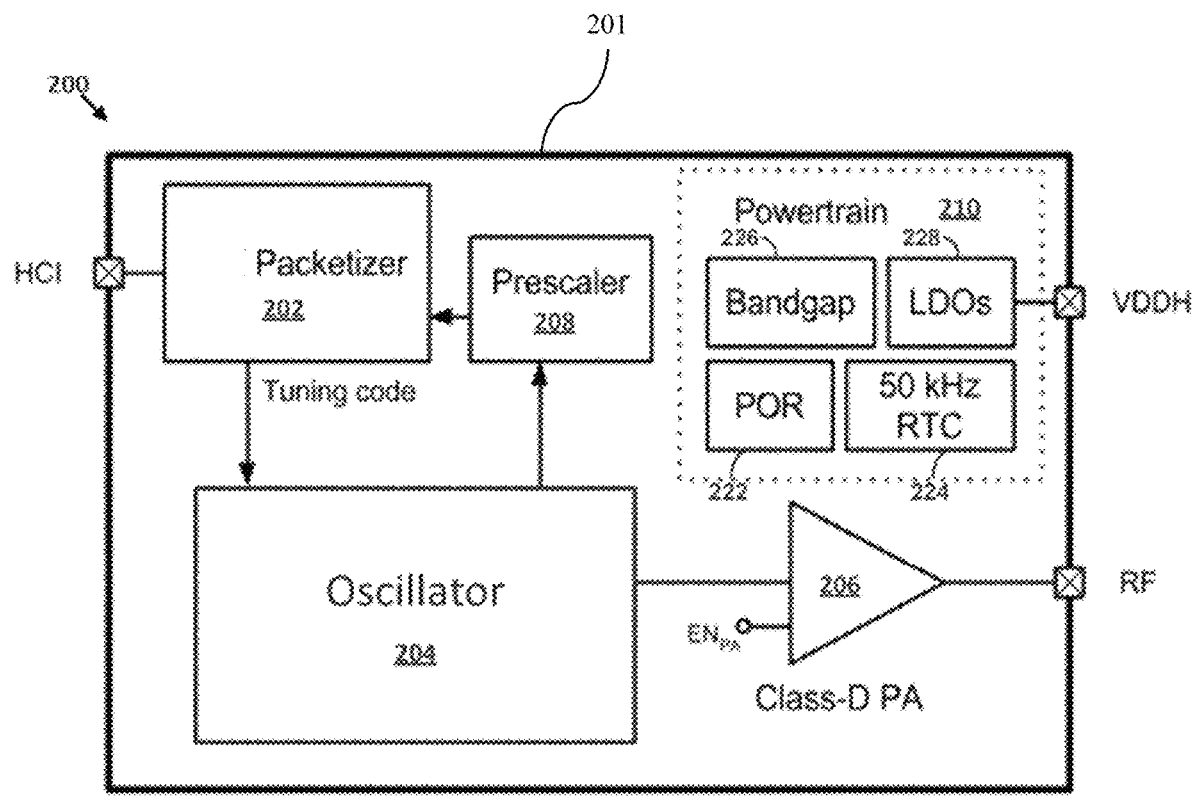
FIG. 2 shows a schematic diagram of an implantable ISM-band transmitter according to an example.

FIG. 2 schematically illustrates an implantable ISM-band transmitter 200, such as an implantable Bluetooth transmitter, according to an example. In some examples, the ISM-band transmitter 200 may be included in other devices as an ISM-band module (such as a Bluetooth module). For instance, a BLE module may be included in or coupled with the beacon 102 in scenario 100. A device, such as beacon 102, that includes an ISM-band module may be referred to as a "host device." Accordingly, an ISM-band module may receive instructions from a processor and/or a memory of a host device. A controller of an ISM-band module may interface with the host stack of its host device via a Host Controller Interface (HCl). For example, ISM-band transmitter 200 may receive a signal via the HCl, which may include data that may be transmitted by the ISM-band transmitter 200. In some examples, the host stack and the controller of an ISM-band module may be implemented on different processors. In other examples, the host stack and the controller of an ISM-band module may be implemented on the same processor.

Still referring to FIG. 2, the ISM-band transmitter 200 may include a hermetically-sealed container 201. The other components of the ISM-band transmitter 200 may internally located within hermetically-sealed container 201. For example, the packetizer 202, oscillator 204, prescaler 208, powertrain 210, amplifier 206, and/or other components may be located inside the hermetically-sealed container 201. In some examples, all the components of ISM-band transmitter 200 may be internally located within hermetically-sealed container 201. Thus, in examples, transmitter 200 does not have any component on the exterior of the hermetically-sealed container 201. For example, transmitter 200 does not have any wire outside of the hermetically-sealed container 201. In such examples, ISM-band transmitter 200 may provide additional safety to a person in which the ISM-band transmitter 200 is implanted. For example, ISM-band transmitter 200 can be magnetic resonance imaging ("MRI")-safe at least because there is no component (such as a wire) outside of hermetically-sealed container 201.

Hermetically-sealed container 201 can be made of one or more metals suitable for implantation in a human body. For example, hermetically-sealed container 201 may be made of titanium, nickel-titanium, stainless steel, cobalt-chrome, another implantable metal, or a combination thereof.

Hermetically-sealed container 201 can have a shape suitable for implantation in a human body. For example, hermetically-sealed container 201 may be cuboidal as shown in hermetically-sealed container 300 in FIGS. 3A and 3B. As another example, hermetically-sealed container 201 may be cylindrical as shown in hermetically-sealed container 400 in FIGS. 4A and 4B. In various examples, hermetically-sealed container 201 may have a cylindrical shape, a spherical shape, a cubical shape, a cuboidal shape, or another suitable shape. In examples, sharp edges and/or corners of the hermetically-sealed container may be beveled to reduce the risk of cutting or puncturing a user when the hermetically-sealed container 201 is implanted in the user.

Hermetically-sealed container 201 can have a size suitable for implantation in a human body. In one example, hermetically-sealed container 201 has a cylindrical shape with a diameter of 30 millimeters and a height of 3 millimeters. In various examples, hermetically-sealed container 201 has a diameter between 10 millimeters and 40 millimeters. In examples, hermetically-sealed container 201 has a length between 20 millimeters and 40 millimeters and a width between 20 millimeters and 40 millimeters. Hermetically-sealed container 201 may have a height between 3 millimeters and 5 millimeters in some examples.

ISM-band transmitter 200 may also include an antenna (not shown in FIG. 2) located inside hermetically-sealed container 201. For example, one or more interior sides of the hermetically-sealed containers can be used as a slot antenna. FIGS. 3A, 3B, 4A, and 4B show examples of implantable hermetically-sealed containers with slots that are configured to act as a far-field radiator. In these examples, the tuning of the impedance, the quality of radiation, and the polarization of the radiation depends on the location and characteristics (e.g., shape, length, width, etc.) of a slot in the hermetically-sealed container. Hermetically-sealed container 300 and/or hermetically-sealed container 400 can be used as hermetically-sealed container 201 in various examples. In various examples, ISM-band transmitter 200 may be a Bluetooth transmitter, a BLE transmitter, an S-band transmitter, or another ISM-band transmitter.

Figure 3A:
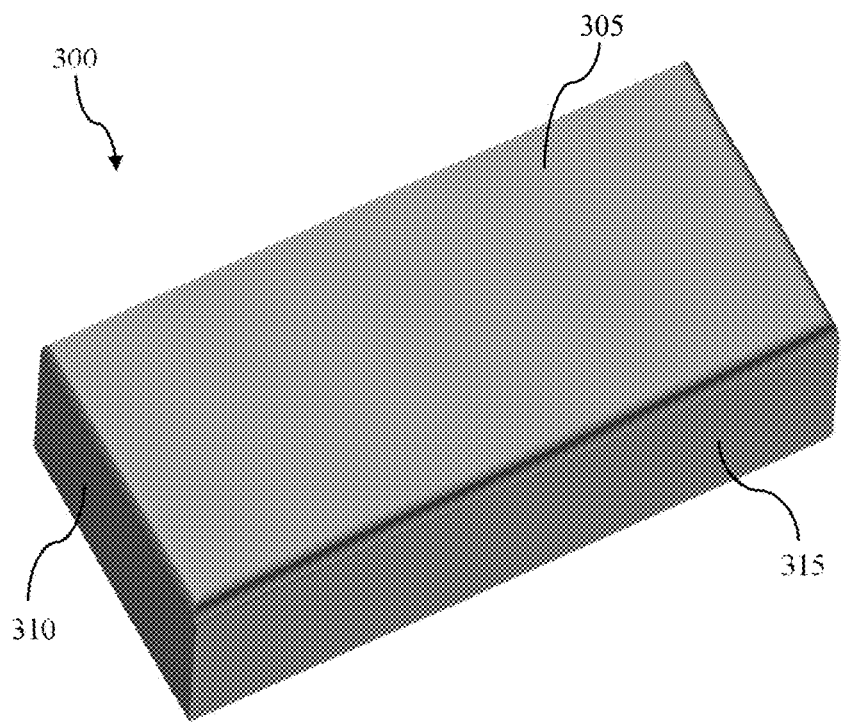
FIGS. 3A and 3B show a hermetically-sealed container according to an example.
Figure 3B:
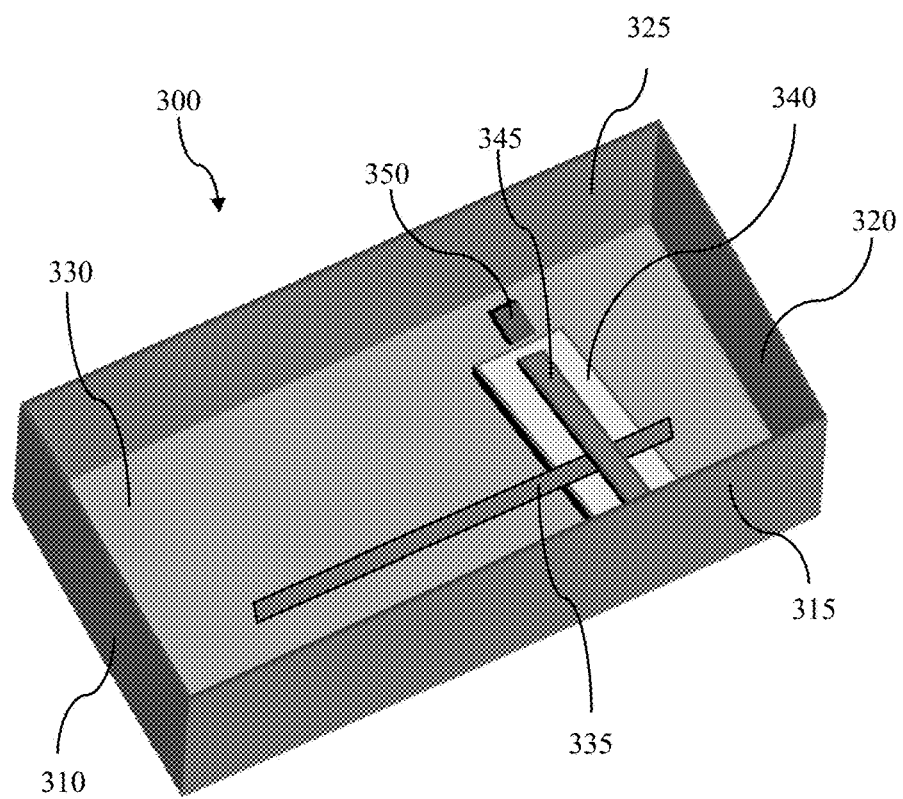

Referring now to FIG. 3A and FIG. 3B, these figures show a hermetically-sealed container 300 according to an example. Hermetically-sealed container 300 has a cuboidal shape and may be made of one or more metals suitable for implantation in a human body such as one or more of the metals discussed above with respect to hermetically-sealed container 201.

In FIG. 3A, an exterior of the hermetically-sealed container 300 is shown. For example, FIG. 3A shows an exterior of surfaces 305, 310, and 315. Other surfaces of the exterior of hermetically-sealed container 300 are not shown in FIG. 3A. In FIG. 3B, surface 305 has been removed to show the inside of hermetically-sealed container 300. For example, FIG. 3B shows an interior of surfaces 320, 325, and 330. Other surfaces of the interior of hermetically-sealed container 300 are not shown in FIG. 3B.

In FIG. 3B, a slot 335, a microwave dielectric substrate 340, a micro-strip transmission line 345, and a transmitter 350 are inside hermetically-sealed container 300 and thus these components are internal to hermetically-sealed container 300.

In FIG. 3B, slot 335 is cut into an interior of surface 330 of hermetically-sealed container 300 and has a width of 500 microns and a length of 22 millimeters. Slot 335 may have a depth less than a thickness of the interior surface 330 of hermetically-sealed container 300. In this example, slot 335 does not need to be filled with a hermitic material, such as a hermitic dielectric material, for container 400 to remain hermetically-sealed. Slot 335 can thus be empty and therefore, in examples, is not filled with any material, such as a hermitic dielectric material, for container 300 to remain hermetically-sealed.

In various examples, slot 335 may have a width between 100 microns and 600 microns and/or a length between 16 millimeters and 28 millimeters. As shown in FIG. 3B, slot 335 crosses micro-strip transmission line 345 towards an end of the micro-strip transmission line 345 and slot 335 is perpendicular to micro-strip transmission line 345. In other examples, slot 335 can cross micro-strip transmission line 345 at any suitable location, such as towards the middle of micro-strip transmission line 345. Slot 335 may not be perpendicular to a micro-strip transmission line in some examples. For example, slot 335 may be positioned at a 75 degree angle to micro-strip transmission line 340 in some examples. The slot can provide a far-field radiator.

Microwave dielectric substrate 340 is located on an interior of surface 330 of hermetically-sealed container 300 in FIG. 3B. Moreover, in FIG. 3B, microwave dielectric substrate 340 is a thermoset microwave material (such as TMM10®) and has a thickness of 0.125 millimeters. In other examples, microwave dielectric substrate 340 may have a thickness between 0.11 millimeters and 0.15 millimeters.

In FIG. 3B, micro-strip transmission line 345 is located on microwave dielectric substrate 340 and is a straight line of copper having a thickness of 0.25 millimeters. In example, microwave dielectric substrate 340 can be any suitable material, such as aluminum oxide, a material that includes aluminum oxide, or another suitable material. In examples, micro-strip transmission line 345 can be any suitable material, such as copper, and can have any suitable shape, such as a straight line, a curved line, a circular line, a spiral line etc. Micro-strip transmission line 345 can have a thickness between 0.2 millimeters and 0.3 millimeters in some examples. As discussed above, micro-strip transmission line 345 is perpendicular to slot 335 in FIG. 3B and can be positioned at any suitable angle to slot 335 in other examples. Hermetically-sealed container 300 can act as a ground plane for micro-strip transmission line 345.

In FIG. 3B, transmitter 350 is located near an end of micro-strip transmission line 345. Transmitter 350 may be a Bluetooth transmitter such as a BLE beacon. In some examples, transmitter 350 can be a beacon discussed herein, such as beacon 102 shown in FIG. 1. Transmitter 350 may have some or all of the internal components (such as packetizer 202, oscillator 204, amplifier 206, prescaler 208, and/or powertrain 210) shown in FIG. 2.

In FIG. 3A and FIG. 3B, hermetically-sealed container 300 does not have any component, such as an electrical component, on the exterior of the hermetically-sealed container 300. Rather, in FIG. 3A and FIG. 3B, every component is inside hermetically-sealed container 300 and thus every component is internal to hermetically-sealed container 300. In this example, the implantable device does not have an antenna external to the hermetically-sealed container 300. Moreover, in this example, the implantable device does not have an inverted F antenna, does not have a monopole antenna, and does not have an electrically small dipole antenna either inside of or outside of hermetically-sealed container 300. Rather, in FIGS. 3A and 3B, hermetically-sealed container 300 provides a slot antenna.

In some examples, hermetically-sealed container 300 has one or more electrical components located on a same plane as micro-strip transmission line 345. For example, one or more components of transmitter 350, a microprocessor (not shown in FIGS. 3A and 3B), and/or a tuning circuit (not shown in FIGS. 3A and 3B) may be located on a same plane as micro-strip transmission line 345. Such electrical component(s) located on a same plane as micro-strip transmission line 345 may increase a gain of the slot antenna.

Figure 4A:
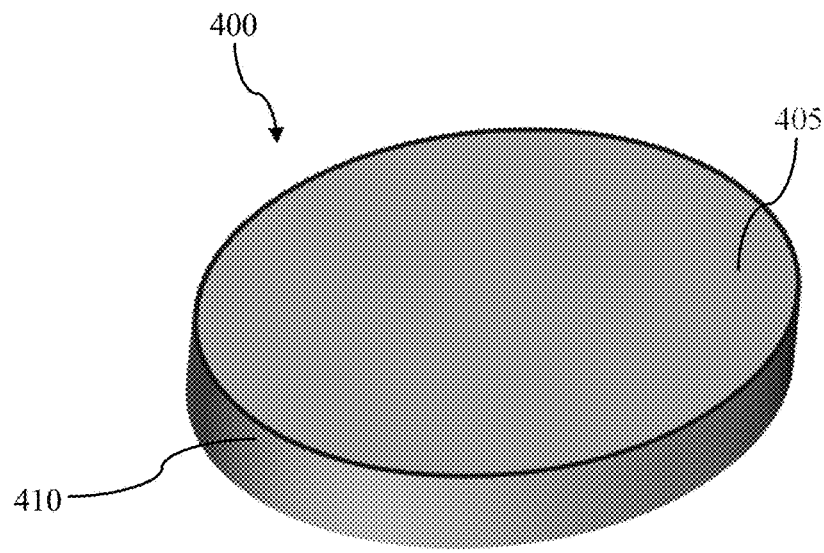
FIGS. 4A and 4B show a hermetically-sealed container according to an example.
Figure 4B:
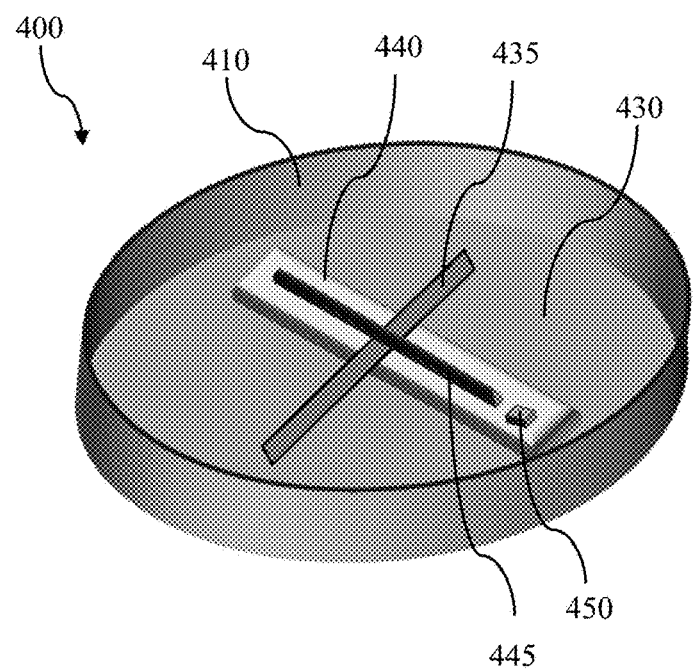

Referring now to FIGS. 4A and 4B, these figures show a hermetically-sealed container 400 according to an example. Hermetically-sealed container 400 has a cylindrical shape and may be made of one or more metals suitable for implantation in a human body such as one or more of the metals discussed above with respect to hermetically-sealed container 201.

In FIG. 4A, an exterior of the hermetically-sealed container 400 is shown. For example, FIG. 4A shows an exterior of surfaces 405 and 410. Other surfaces of the exterior of hermetically-sealed container 400 are not shown in FIG. 4A. In FIG. 4B, surface 405 has been removed to show the inside of hermetically-sealed container 400. For example, FIG. 4B shows an interior of surfaces 410 and 430. Other surfaces of the interior of hermetically-sealed container 400 are not shown in FIG. 4B. In FIG. 4B, a slot 435, a microwave dielectric substrate 440, a micro-strip transmission line 445, and a transmitter 450 are inside hermetically-sealed container 400 and thus these components are internal to hermetically-sealed container 400.

In FIG. 4B, slot 435 has a width of 127 microns and a length of 20 millimeters cut into an interior of surface 430 of hermetically-sealed container 400. Slot 435 may have a depth less than a thickness of the interior surface 430 of hermetically-sealed container 400. In this example, slot 435 does not need to be filled with a hermitic material, such as a hermitic dielectric material, for container 400 to remain hermetically-sealed. Slot 435 thus can be empty and therefore, in examples, is not filled with any material, such as a hermitic dielectric material, for container 400 to remain hermetically-sealed.

In various examples, slot 435 may have a width between 100 microns and 600 microns and/or a length between 16 millimeters and 28 millimeters. As shown in FIG. 4B, slot 435 crosses micro-strip transmission line 445 in a middle of the micro-strip transmission line 445 and slot 435 is perpendicular to micro-strip transmission line 445. In other examples, slot 435 can cross micro-strip transmission line 445 at any suitable location, such as towards an end of micro-strip transmission line 445. Slot 435 may not be perpendicular to a micro-strip transmission line in some examples. For example, slot 435 may be positioned at a 85 degree angle to micro-strip transmission line 445 in some examples. Slot 435 can provide a far-field radiator.

Microwave dielectric substrate 440 is located on an interior of surface 430 of hermetically-sealed container 400 in FIG. 4B. Moreover, in FIG. 4B, microwave dielectric substrate 440 is a thermoset microwave material (such as TMM10®) and has a thickness of 0.14 millimeters. In other examples, microwave dielectric substrate 440 may have a thickness between 0.11 millimeters and 0.15 millimeters.

In FIG. 4B, micro-strip transmission line 445 is located on microwave dielectric substrate 440, such as aluminum oxide, and is a straight line having a thickness of 0.25 millimeters. In other examples, micro-strip transmission line 445 can be any suitable material, such as copper, and can have any suitable shape, such as a straight line, a curved line, a circular line, a spiral line etc. Micro-strip transmission line 445 can have a thickness between 0.2 millimeters and 0.3 millimeters in some examples. As discussed above, micro-strip transmission line 445 is perpendicular to slot 435 in FIG. 4B and can be positioned at any suitable angle to slot 435 in other examples. Hermetically-sealed container 400 can act as a ground plane for micro-strip transmission line 445.

In FIG. 4B, transmitter 450 is located near an end of micro-strip transmission line 445. Transmitter 450 may be a Bluetooth transmitter such as a BLE beacon. In some examples, transmitter 450 can be a beacon discussed herein, such as beacon 102 shown in FIG. 1. Transmitter 450 may have some or all of the internal components (such as packetizer 202, oscillator 204, amplifier 206, prescaler 208, and/or powertrain 210) shown in FIG. 2.

In FIG. 4A and FIG. 4B, hermetically-sealed container 400 does not have any component, such as an electrical component, on the exterior of the hermetically-sealed container 400. Rather, in FIG. 4A and FIG. 4B, every component is inside hermetically-sealed container 400 and thus every component is internal to hermetically-sealed container 400. In this example, the implantable device does not have an antenna external to the hermetically-sealed container 400. Moreover, in this example, the implantable device does not have an inverted F antenna, does not have a monopole antenna, and does not have an electrically small dipole antenna either inside of or outside of hermetically-sealed container 400. Rather, in FIGS. 4A and 4B, hermetically-sealed container 300 provides a slot antenna.

In some examples, hermetically-sealed container 400 has one or more electrical components located on a same plane as micro-strip transmission line 445. For example, one or more components of transmitter 450, a microprocessor (not shown in FIGS. 4A and 4B), and/or a tuning circuit (not shown in FIGS. 4A and 4B) may be located on a same plane as micro-strip transmission line 445. Such electrical component(s) located on a same plane as micro-strip transmission line 445 may increase a gain of the slot antenna.

In examples, a transmitter may have a packetizer, an oscillator, a powertrain, and/or an amplifier. For example, referring back to FIG. 2, the ISM-band transmitter 200 may include a packetizer 202, an oscillator 204, a powertrain 210, and an amplifier 206. These components, as described herein, may be used to transmit a signal 104 from ISM-band transmitter 200 (such as a BLE transmitter). Accordingly, in some examples, an ISM-band module (such as a BLE module) includes only a transmitter as a communication interface. Such a module may operate solely as a transmitter (also referred to herein as a "broadcaster"). For instance, in scenario 100, the beacon 102, using an ISM-band transmitter, may transmit a signal, which may be received by the computing devices 106 and 108, without pairing with or receiving a signal from the computing devices.

In other examples, the ISM-band transmitter 200 (such as a BLE transmitter) may operate as a transmitter of a transceiver device. A transceiver device may include components that may be used to transmit and receive a signal. For instance, the transceiver may include, along with the one or more of the other transmitter components described herein, a low-noise amplifier (LNA), a mixer (e.g., 1/Q mixer), a local oscillator (LO), a variable gain amplifier, filters (e.g., baseband filter), and an analog-digital-converter (ADC). The transceiver may also include an antenna that may be used to transmit and receive signals. For instance, in scenario 100, the beacon 102, using an ISM-band transceiver (such as a BLE transceiver), may transmit a signal, which may be received by the computing devices 106 and 108. The beacon 102 may also receive a signal from the computing devices 106 and 108 in some examples.

Returning to FIG. 2, the packetizer 202 may receive a signal via the HCl. As explained elsewhere herein, the signal may originate from a processor of a host device. Further, the received signal may include packet data that may be included in the signal transmitted by the ISM-band transmitter 200. The received signal may also include data indicative of a configuration of the ISM-band module. For example, the received signal may include parameters, such as encryption parameters, modulation parameters, a mode of operation of the ISM-band module, packet type, etc. The received parameters may be used to configure the ISM-band module to generate a signal, which may be transmitted by the antenna.

For instance, the signal received via the HCl may be indicative of a mode of operation of the ISM-band module. Within examples, the mode of operation may depend on the functionality of the ISM-band module. In some examples, the functionality of an ISM-band module may be predetermined and fixed, as the ISM-band module may be used in a single application. In other instances, a user may provide an input indicative of the mode of operation to the host computing device. In particular, the user may provide an input to an input/output function of the computing device, possibly a graphical user-interface (GUI), to specify the mode of operation.

In some examples, the modes of operation of the ISM-band transmitter 200 may include an advertising mode in which an advertising protocol is used to periodically transmit data packets referred to as advertising packets (also referred to herein as "advertisement packets"). Despite their name, these data packets typically have no relation to "advertisements" in the marketing sense of the word. Rather, such data packets are referred to as advertising packets because they may be used to announce various data to one or more other devices capable of receiving the announcement. The advertising packets may carry data indicative of the ISM-band transmitter 200 (e.g., a unique identification number (UID)). Alternatively or additionally, advertising packets may carry data indicative of or information from a device that may include the ISM-band transmitter 200 as a Bluetooth module. For example, the host device may use advertising packets to possibly "pair" or connect with another device.

In another example, an ISM-band module may use advertising packets to advertise data, such as biological data, which may have been stored in a memory of its host device. The beacon 102 may use an ISM-band module to broadcast a signal that may provide one of the computing devices with biological information of a user in which the beacon 102 is implanted. In yet other examples, an ISM-band module may be used to transmit advertising packets, which may include data that may have been collected by the host device. For example, the advertising packets may include biological data gathered by a sensor of the host device.

Furthermore, in some instances, the mode of operation of an ISM-band module may affect its power consumption. For example, an ISM-band module may decrease its power consumption by using advertising protocols. Advertising protocols may maintain the low power consumption of an ISM-band module by periodically broadcasting a signal during certain time intervals. During time intervals when an ISM-band module is not broadcasting a signal, the ISM-band module may idle in a standby mode. Alternatively, the ISM-band module may turn off. Accordingly, by turning on only when transmitting a signal in an active transmit mode, an ISM-band module may decrease its power consumption, which may be advantageous for devices with a finite power source. As such, advertising protocols are designed to allow an ISM-band module to advertise data to one or more computing devices while maintaining the low power consumption.

Furthermore, ISM-band protocols (such as BLE protocols) may include different types of advertising packets. The advertising packet type may at least specify a configuration of an ISM-band module. For instance, the advertising packet type may specify whether the ISM-band module is connectable and/or scannable. A connectable ISM-band module may pair with another ISM-band device, and a scannable ISM-band module may transmit a data packet in response to receiving a scan request from another ISM-band device. For example, a connectable Bluetooth module may pair with another Bluetooth device, and a scannable BLE module may transmit a data packet in response to receiving a scan request from another Bluetooth device. Furthermore, an advertising packet may be a directed packet. A directed packet may include a BLE module's address and the receiver device's address, whereas an undirected packet may not be directed toward a particular receiver.

In some examples, an ISM-band module may include only the ISM-band transmitter 200 and, therefore, may not be able to operate in a connectable configuration. Furthermore, the ISM-band transmitter 200 may not be able to receive scan requests from other devices, such as other ISM-band devices. Accordingly, in some examples, an ISM-band module may operate in a non-connectable and non-scannable configuration in order to decrease power consumption. However, in other examples, an ISM-band module may include a transceiver. In such examples, the ISM-band module may operate in a connectable and/or a scannable configuration.

In some examples, such as where an ISM-band module is a BLE module, there can be advantages to using BLE advertising protocols in addition to low power consumption of the BLE module operating in accordance with advertising protocols. For example, in scenario 100, the computing devices 106 and 108 may discover Bluetooth devices located near the computing device faster (and consuming less energy) using advertising protocols than by using other protocols. As described elsewhere herein, advertising protocols may use three fixed channels of a wireless spectrum, e.g., the 2.4 GHz wireless spectrum. Thus, the computing devices 106 and 108 may detect other Bluetooth devices by only scanning the three fixed channels, rather than scanning a broad wireless spectrum, which may allow for receiving and sending BLE advertisement packets faster than other protocols.

Returning to FIG. 2, the packetizer 202 may use the data included in the signal received via the HCl to generate a data signal, which may include one or more data packets. Accordingly, the packetizer 202 may receive instructions to generate a data signal including one or more data packets according to the advertising protocol. Further, the instructions may detail the type of advertising packet to broadcast. For instance, as explained above, the type of advertising packet may determine whether an ISM-band module is connectable and/or scannable, and/or whether the packet is directed. In an example, the packetizer 202 may receive data indicative of instructions to generate a data signal that includes a non-connectable, non-scannable, and undirected advertising packet. In another example, the packetizer 202 may receive data indicative of instructions to generate a data signal that includes a scannable and undirected advertising packet.

Returning to FIG. 2, the oscillator 204 may generate an RF carrier signal that may carry the data signal generated by the packetizer 202. The RF signal carrying the data may then be broadcast by an antenna. For example, the RF signal may be broadcast to a slot antenna internal to the hermetically-sealed container. In one example, the RF signal is broadcast to a slot antenna provided by slot 335 shown in FIG. 3B. In another example, the RF signal is broadcast to a slot antenna provided by slot 435 shown in FIG. 4B. The antenna may broadcast the RF signal to an external computing device. For example, referring to FIG. 5, a slot antenna internal to a hermetically-sealed container in implantable device 510 can broadcast the RF signal to smartphone 520 in one example. In one example, such as where the ISM-band transmitter is a BLE transmitter, the RF signal broadcast from the slot antenna in implantable device 510 to smartphone 520 may have a frequency between 2400 MHz and 2483.5 MHz. In various example, an RF signal can be broadcast from the slot antenna in an implantable device to an external computing device and the RF signal may have a frequency within the ISM-band (e.g., 13.553 MHz-13.567 MHz, 26.957 MHz-27.283 MHz, 40.66 MHz-40.7 MHz, 433.05 MHz-434.79 MHz, 902 MHz-928 MHz, 2.4 GHz-2.5 GHz, 5.725 GHz-5.875 GHz, etc.).

As illustrated in FIG. 2, the oscillator 204 may be a free-running oscillator (such as a Pierce oscillator and/or a Colpitts oscillator), which may be used to directly generate an RF carrier signal. Thus, a free-running oscillator may replace a frequency synthesizer (e.g., Phase Locked Loop (PLL) synthesizer) to generate an RF carrier signal. Using a free-running oscillator may result in considerable power savings as compared to using a frequency synthesizer, which may be advantageous for low power devices. In other examples, a frequency synthesizer (such as a PLL synthesizer) may generate an RF carrier signal.

Further, both the turn-on time for the frequency synthesizer to lock to its frequency reference and the turn-on time of its frequency reference circuit may be significant compared to the packet duration. Therefore, the turn-on time (i.e., the time to go from sleep mode to active transmit mode) for a transmitter using a frequency synthesizer may be greater than a transmitter using a free-running oscillator. A longer turn-on time may result in greater power dissipation. Accordingly, using the free-running oscillator, which may have a reduced turn-on time compared to a frequency synthesizer, may result in further power savings.

A free-running oscillator and/or a frequency synthesizer may directly generate the RF carrier signal, which may have a frequency within a wireless spectrum, e.g., the 2.4 GHz wireless spectrum. Within examples, a free-running oscillator and/or a frequency synthesizer may directly generate an RF carrier signal that has a frequency of one of the three channels in the 2.4 GHz band that are allocated to BLE advertising protocols according to Bluetooth specifications. The three "advertisement channels" are specified as 1 MHz wide channels with frequencies of 2.402 GHz, 2.480 GHz, and 2.426 GHz.

Note that the example oscillator provided in FIG. 2 and the accompanying description herein is for illustrative purposes only and should not be considered limiting. For instance, the ISM-band transmitter 200 may include more than one free-running oscillator. In an example, the ISM-band transmitter 200 may include three free-running oscillators, each of which may be used to generate a carrier signal at a frequency of the three BLE channels. In such examples, the ISM-band transmitter 200 may utilize methods such as multichannel transmission and frequency hopping.

In examples, a free-running oscillator may include a resonator, among other components (such as a transistor, a biasing resistor, a capacitor, etc.). The resonator, which may be located off of the IC of the ISM-band transmitter 200, may be used as a filter to filter the oscillation frequency. In various examples, a resonator in ISM-band transmitter 200 can be any suitable resonator, such as a high frequency resonator which may provide an oscillation frequency with a stability and an accuracy that may meet Bluetooth standards. In some examples, the resonator may be a crystal resonator. In another examples, the resonator may be a quartz resonator. In yet other examples, the resonator can be a thin-film bulk acoustic resonator ("FBAR").

As noted above, the RF carrier signal generated by the oscillator 204 may be used to carry the data signal generated by the packetizer 202. More specifically, the data signal generated by the packetizer 202 may act as a tuning code, which may have a specific symbol rate. Further, the tuning code may be used to directly modulate the RF carrier signal. Accordingly, the modulated RF carrier signal may carry the data signal generated by the packetizer 202. Within examples, the tuning code may modulate the RF carrier signal according to at least BLE protocols.

For instance, BLE protocols specify using Gaussian Frequency Shift Keying (GFSK) as the modulation scheme to modulate the RF carrier signal. Accordingly, the tuning code may be used to modulate the RF carrier signal to two different frequencies of the same advertising channel according to GFSK. Additionally and/or alternatively, the tuning code may be used to modulate the RF carrier signal to two different frequencies of the same advertising channel according to Binary Frequency Shift Keying (BFSK). The oscillator 204 may include a bank or an array of switched capacitors, which may be used to adjust the load capacitance of the oscillator 204. As explained above, adjusting the load capacitance of the oscillator 204 may adjust the oscillation frequency. The digital data signal, indicative of digital "0" and "1," may be used to modify the load capacitance of the oscillator 204, such that the oscillator 204 may generate a modulated signal of two frequencies, one of which corresponds to digital "0" and the other to digital "1."

The modulated RF signal, carrying the data signal, may be transmitted to a class-D power amplifier 206 as illustrated in FIG. 2. However, also note that at least a portion of the modulated signal may be transmitted to a prescaler 208. The prescaler 208 may scale the signal and provide the scaled signal to the packetizer 202, where it may be used as a clock source. For instance, the prescaler 208 may scale down the 2.48 GHz signal to a 1 MHz or 8 MHz signal. By using a portion of the carrier signal as a clock source for the packetizer 202, there may be no need for a separate timing source for the packetizer 202, thereby further increasing power savings.

Furthermore, as illustrated in FIG. 2, the modulated RF carrier signal may be amplified using the class-D power amplifier 206. The amplified signal may then be transmitted to the antenna (represented as "RF" in FIG. 2) where it may be broadcast over the air. As explained above, in some examples, an ISM-band module may be operating in an advertising mode, which involves the ISM-band module periodically transmitting advertising packets. Accordingly, the broadcast RF signal may include advertisement packets, which may be received by one or more ISM-band devices.

An ISM-band module may be powered by the powertrain 210. The powertrain may include a low dropout regulator (LDO) 228, a power on reset (PoR) 222, a bandgap voltage reference (Bandgap) 226, and a real time clock (RTC) 224. Note that the RTC 224 may have a low frequency and may operate without a crystal reference, as the packetizer 202 may use a signal from the oscillator 204 as explained above. In other examples, RTC 224 may operate with a crystal reference.

Figure 5:
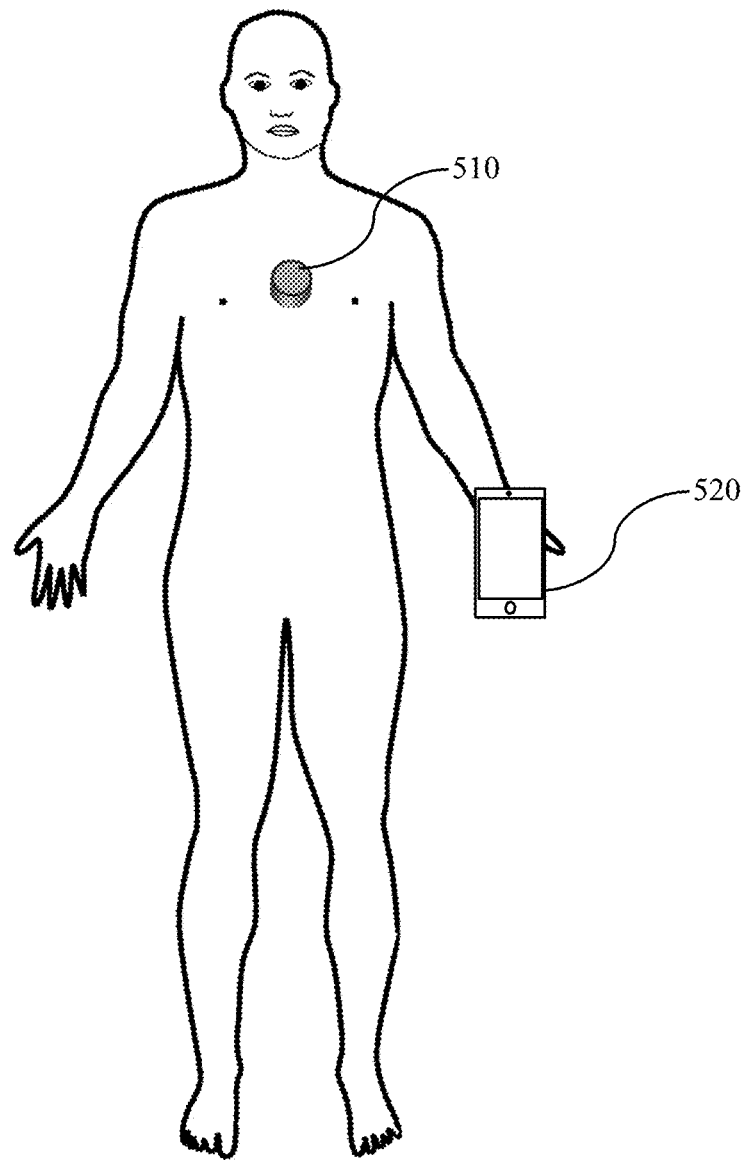
FIG. 5 shows an example system for in-body ISM-band transmission according to an example.

Referring now to FIG. 5, this figure shows an example implantable device 510 implanted in a user's chest. In examples, implantable device 510 may be a device discussed herein, such as beacon 102 discussed herein with respect to FIG. 1, and/or ISM-band transmitter 200 discussed herein with respect to FIG. 2. In some examples, implantable device 510 may have a hermetically-sealed container, such as hermetically-sealed container 300 discussed herein with respect to FIG. 3 and/or hermetically-sealed container 400 discussed herein with respect to FIG. 4. In one example, all of the components of implantable device 510 is internal to the hermetically-sealed container.

As shown in FIG. 5, implantable device 510 is implanted in a user's chest. In other examples, implantable device 510 may be implanted in any suitable location in a user's body such as a user's shoulder, arm, abdomen, thigh, calf, etc. Implantable device 510 can be implanted at any suitable depth such that an RF signal can be broadcast by implantable device 510 to an external computing device (such as a smartphone, tablet, etc.) at an appropriate location. For example, implantable device 510 may be implanted 3 millimeters below a skin surface in a user's chest such that implantable device 510 can broadcast an RF signal to smartphone 520 held in the user's hand(s). As another example, implantable device 510 may be implanted 3 millimeters below a muscle surface of a muscle (such as an abdominal muscle, a bicep muscle, a gluteus muscle, a hamstring muscle, etc.) of a user and the implantable device 510 may broadcast an RF signal to an external computing device near the user. In various examples, implantable device 510 is configured to be implanted between 1 and 10 millimeters below a skin surface and/or a muscle surface of a user and the implantable device 510 is configured to broadcast an RF signal to an external computing device when implanted. In examples, an RF signal broadcast by implantable device 510 has an industrial, scientific, and medical radio ("ISM")-band compatible frequency. For example, the RF signal broadcast by implantable device 510 can be a Bluetooth-compatible frequency.

While some examples of devices, systems, and methods herein are described in terms of software executing on various machines, the devices, systems, and methods may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable computing devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

That which is claimed is:

1. An implantable industrial, scientific, and medical (ISM)-band device comprising:
    a hermetically-sealed container constructed of an electrically conductive material, the hermetically-sealed container defining a slot antenna;
    an ISM-band transmitter disposed within the hermetically-sealed container;
    a microwave dielectric substrate disposed on an interior surface of the hermetically-sealed container corresponding to the slot antenna; and
    a micro-strip transmission line disposed on the microwave dielectric substrate and crossing the slot antenna.

2. The implantable ISM-band device of claim 1, wherein the ISM-band transmitter is a Bluetooth Low Energy (BLE) transmitter.

3. The implantable ISM-band device of claim 2, wherein the slot is configured to transmit a radio frequency (RF) signal from the BLE transmitter to an external computing device at a frequency between 2400 MHz and 2483.5 MHz.

4. The implantable ISM-band device of claim 1, wherein the ISM-band transmitter is positioned near an end of the micro-strip transmission line.

5. The implantable ISM-band device of claim 1, wherein the hermetically-sealed container is cylindrical and comprises a diameter between 10 millimeters and 40 millimeters.

6. The implantable ISM-band device of claim 5, wherein the hermetically-sealed container comprises a height between 3 millimeters and 5 millimeters.

7. The implantable ISM-band device of claim 1, wherein the micro-strip transmission line comprises copper deposited on the microwave dielectric substrate.

8. The implantable ISM-band device of claim 1, wherein the microwave dielectric substrate comprises aluminum oxide.

9. The implantable ISM-band device of claim 1, wherein the microwave dielectric substrate comprises a thickness between 0.11 millimeters and 0.15 millimeters.

10. The implantable ISM-band device of claim 9, wherein the micro-strip transmission line comprises a thickness between 0.2 millimeters and 0.3 millimeters.

11. The implantable ISM-band device of claim 1, wherein the slot comprises a width between 100 microns and 600 microns.

12. The implantable ISM-band device of claim 1, wherein the slot comprises a width between 120 microns and 140 microns.

13. The implantable ISM-band device of claim 1, wherein the slot comprises a length between 16 millimeters and 28 millimeters.

14. The implantable ISM-band device of claim 1, wherein the slot is substantially perpendicular to the micro-strip transmission line.

15. The implantable ISM-band device of claim 14, wherein the slot crosses the micro-strip transmission line at a middle of the micro-strip transmission line.

16. The implantable ISM-band device of claim 14, wherein the slot crosses the micro-strip transmission line towards an end of the micro-strip transmission line.

17. The implantable ISM-band device of claim 1, wherein the electrically conductive material comprises titanium.

18. The implantable ISM-band device of claim 1, wherein the hermetically-sealed container provides a ground plane for the micro-strip transmission line, and wherein the slot provides a far-field radiator.

19. The implantable ISM-band device of claim 1, wherein the implantable device does not comprise an inverted F antenna, does not comprise a monopole antenna, and does not comprise an electrically small dipole antenna.

20. A system comprising:
an implantable industrial, scientific, and medical (ISM)-band device comprising:
a hermetically-sealed container constructed of an electrically conductive material, the hermetically-sealed container defining a slot antenna;
an ISM-band transmitter disposed within the hermetically-sealed container;
a microwave dielectric substrate disposed on an interior surface of the hermetically-sealed container corresponding to the slot antenna;
a micro-strip transmission line disposed on the microwave dielectric substrate and crossing the slot antenna, wherein the hermetically-sealed container acts as a ground plane for the micro-strip transmission line;
and
a sensor.

21. The system of claim 20, wherein the ISM-band transmitter is a Bluetooth Low Energy (BLE) transmitter and the RF signal comprises a frequency between 2400 MHz and 2483.5 MHz.

22. The system of claim 20, wherein the hermetically-sealed container is cylindrical and comprises a diameter between 10 millimeters and 40 millimeters.

23. The system of claim 22, wherein the hermetically-sealed container comprises a height between 3 millimeters and 5 millimeters.

24. The system of claim 20, wherein the micro-strip transmission line comprises copper deposited on the microwave dielectric substrate.

25. The system of claim 20, wherein the microwave dielectric substrate comprises aluminum oxide.

26. The system of claim 20, wherein the microwave dielectric substrate comprises a thickness between 0.11 millimeters and 0.15 millimeters.

27. The system of claim 26, wherein the micro-strip transmission line comprises a thickness between 0.2 millimeters and 0.3 millimeters.

28. The system of claim 20, wherein the slot comprises a width between 100 microns and 600 microns.

29. The system of claim 20, wherein the slot comprises a width between 120 microns and 140 microns.

30. The system of claim 20, wherein the slot comprises a length between 16 millimeters and 28 millimeters.

31. The system of claim 20, wherein the slot is substantially perpendicular to the micro-strip transmission line.

32. The system of claim 31, wherein the slot crosses the micro-strip transmission line at a middle of the micro-strip transmission line.

33. The system of claim 31, wherein the slot crosses the micro-strip transmission line towards an end of the micro-strip transmission line.

34. The system of claim 20, wherein the electrically conductive material comprises titanium.

35. The system of claim 20, wherein the sensor comprises at least one of a temperature sensor, a pressure sensor, an oxygen sensor, or a pH sensor.

* * * * *